United States Patent
Luo

(10) Patent No.: US 11,220,627 B2
(45) Date of Patent: Jan. 11, 2022

(54) THERMALLY ACTIVATED DELAYED FLUORESCENT MONOMOLECULAR WHITE LIGHT MATERIAL, METHOD OF MANUFACTURING THEREOF, AND ORGANIC ELECTROLUMINESCENCE DEVICE

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 519 days.

(21) Appl. No.: 16/333,270

(22) PCT Filed: Feb. 28, 2019

(86) PCT No.: PCT/CN2019/076409
§ 371 (c)(1),
(2) Date: Mar. 14, 2019

(87) PCT Pub. No.: WO2020/082656
PCT Pub. Date: Apr. 30, 2020

(65) Prior Publication Data
US 2020/0123440 A1 Apr. 23, 2020

(51) Int. Cl.
*C09K 11/06* (2006.01)
*C07D 417/14* (2006.01)
(Continued)

(52) U.S. Cl.
CPC ............ *C09K 11/06* (2013.01); *C07D 417/14* (2013.01); *C07F 7/083* (2013.01); *C07F 7/0816* (2013.01);
(Continued)

(58) Field of Classification Search
CPC ............ C09K 11/06; C09K 2211/1018; C07D 257/08; C07D 403/14; C07D 417/14;
(Continued)

(56) References Cited

FOREIGN PATENT DOCUMENTS

| CN | 101386602 A | 3/2009 |
|---|---|---|
| CN | 105481794 A | 4/2016 |

(Continued)

OTHER PUBLICATIONS

Computer-generated English-language translation of CN-108219781-A.*

(Continued)

*Primary Examiner* — Vu A Nguyen
(74) *Attorney, Agent, or Firm* — Mark M. Friedman

(57) ABSTRACT

A thermally activated delayed fluorescent monomolecular white light material, a method of synthesizing thereof, and an organic electroluminescent device. The material includes a raw material containing a first group, a raw material containing a second group, and 3,3'-dibromo-1,5,1',5'-tetramethyl-1,2,4,5-homotetradecene. The thermally activated delayed fluorescent monomolecular white light material synthesis method comprises: a first mixed solution preparation step, a first extraction step, a second mixed solution preparation step, and a second extraction step. A light emitting layer of the organic electroluminescent device includes the thermally activated delayed fluorescent monomolecular white light material.

10 Claims, 1 Drawing Sheet

(51) Int. Cl.
    *C07D 403/14*     (2006.01)
    *C07F 7/08*     (2006.01)
    *H01L 51/00*     (2006.01)
    *H01L 51/50*     (2006.01)

(52) U.S. Cl.
    CPC ...... *H01L 51/0067* (2013.01); *H01L 51/0072* (2013.01); *C09K 2211/1018* (2013.01); *H01L 51/5012* (2013.01)

(58) Field of Classification Search
    CPC .... C07F 7/0816; C07F 7/083; H01L 51/0067; H01L 51/0072; H01L 51/5012
    See application file for complete search history.

(56) References Cited

FOREIGN PATENT DOCUMENTS

| CN | 108219781 A | * | 6/2018 | ........... C07D 413/04 |
| WO | 2015121241 A1 | | 8/2015 | |

OTHER PUBLICATIONS

Zongliang Xie, et al. White-Light Emission Strategy of a Single Organic Compound with Aggregation-Induced Emission and Delayed Fluorescence Properties, Angew. Chem. Int. Ed. 2015, 54, 7181-7184.

* cited by examiner

THERMALLY ACTIVATED DELAYED FLUORESCENT MONOMOLECULAR WHITE LIGHT MATERIAL, METHOD OF MANUFACTURING THEREOF, AND ORGANIC ELECTROLUMINESCENCE DEVICE

CROSS REFERENCE TO RELATED APPLICATION

This application claims the priority of International Application No. PCT/CN2019/076409, filed on 2019 Feb. 28, which claims priority to Chinese Application No. 201811238683.9, filed on 2018 Oct. 23. The entire disclosures of each of the above applications are incorporated herein by reference.

BACKGROUND OF INVENTION

Field of Invention

The present invention relates to the field of organic electroluminescence technologies, and in particular, to a thermally activated delayed fluorescent monomolecular white light material, a method of manufacturing thereof, and an organic electroluminescence device.

Description of Prior Art

Photoelectric conversion efficacy is one of the most important parameters for evaluating organic light emitting diodes (OLEDs). After the advent of OLED displays, various phosphor-based and fluorescent-based luminescent material systems have been developed to improve the luminous efficacy of OLEDs. Fluorescent-based OLEDs have high stability, but are limited by the law of quantum statistics. Under electrical activation, the ratio of single-excited excitons to triple-excited excitons is 1:3. Therefore, the internal electroluminescence quantum efficacy of the fluorescent material is limited to 25%. A phosphorescent material has a spin-or-coupling effect of heavy atoms, and can simultaneously utilize single-excited excitons and triple-excited excitons. The theoretical intra-electron luminescence quantum efficacy of the phosphorescent material can reach 100%. However, phosphor-based OLED materials use precious metals, which are costly on the one hand and not environmentally friendly on the other hand.

Most of the current researches focus on vapor-deposited materials, which make the fabrication cost of the devices very high. Polymer thermal activation delayed fluorescent materials have obvious advantages in wet processing due to good film formation. However, how to make thermal activation retardation fluorescent polymers maintain a high photoluminescence quantum yield and a large reverse intersystem enthalpy constant has not been solved. This is also the reason why the quantum efficacy of devices prepared by the polymer thermal activation delayed fluorescent materials is relatively low.

In an organic electroluminescent device, a dominant function is the light emitting layer, and the performance of a light emitting material is a key factor determining the performance of the device. In conventional small molecule white light doping devices, their main bodies of the light emitting layers are fabricated by simple physical doping, in which phase separation is unavoidable, and charge transfer complexes and exciplexes are easily formed, thereby affecting the performance of the device. A white light polymer luminescent material has a main chain as a main body, and side chains link luminescent objects of different wavelengths to form a luminescent system, which can effectively avoid phase separation. However, a molecular structure of the white light polymer is uncertain, the repeatability of the synthesis is poor, and the luminous efficacy is low, which greatly limits its application.

Technical Problem

The present invention aims to provide a thermally activated delayed fluorescent monomolecular white light material, a method of manufacturing thereof, and an organic electroluminescence device, and to solve the problems that the molecular structure of the white light polymer is uncertain, the repeatability of the synthesis is poor, and the luminous efficacy is low.

SUMMARY OF INVENTION

The present invention provides a thermally activated delayed fluorescent monomolecular white light material, wherein the thermally activated delayed fluorescent monomolecular white light material is obtained by synthesizing a raw material containing a first group, another raw material containing a second group and 3,3'-dibromo-1,5,1',5'-tetramethyl-1,2,4,5-homotetradecene, and a structural of the thermally activated delayed fluorescent monomolecular white light material is:

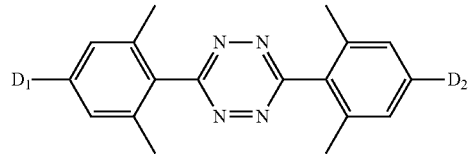

wherein, D1 is the first group, D2 is the second group, and the first group and the second group are asymmetric groups.

Further, in the structural, raw materials of the first group and the second group are selected from one of 9,9'-diphenylsilyl acridine, iminoguanidine, 3,6-dimethyl-spirosilane acridine, 3,6-dimethylcarbazole and phenothiazine or acridone.

To obtain the thermally activated delayed fluorescent monomolecular white light material, the present invention also provide a method for synthesizing a thermally activated delayed fluorescent monomolecular white light material, comprising the steps of: a first mixed solution preparation step, comprising placing a raw material of a first group, 3,3'-dibromo-1,5,1',5'-tetramethyl-1,2,4,5-homotetradecene and a catalyst in a reaction vessel to be fully reacted to obtain a first mixed solution, wherein the first mixed solution comprises the raw material of the first group and an intermediate formed by the reaction of 3,3'-dibromo-1,5,1',5'-tetramethyl-1,2,4,5-homotetradecene; a first extraction step, comprising cooling the first mixed solution to room temperature to extract the mixed solution and obtain the intermediate; a second mixed solution preparation step, comprising placing a raw material of a second group, the intermediate and a catalyst in a reaction vessel to obtain a second mixed solution, wherein the second mixed solution comprises the intermediate and the raw material of the second group; a second extraction step, comprising cooling the second mixed solution to the room temperature, wherein the second mixed solution is extracted to obtain a target compound, and the target compound is isolated and purified to obtain the thermally activated delayed fluorescent monomolecular white light material.

Further, raw materials of the first group and the second group are selected from one of 9,9'-diphenylsilyl acridine, iminoguanidine, 3,6-dimethyl-spirosilane acridine, 3,6-dimethylcarbazole and phenothiazine or acridone; and a molar ratio of the raw material of the first group to 3,3'-dibromo-1,5,1',5'-tetramethyl-1,2,4,5-homotetradecene ranges from 1:1 to 1:5, and a molar ratio of the raw material of the second group to the intermediate ranges from 1:1 to 1:5.

Further, in the first mixed solution preparation step, a reaction time is 24 hours, and a reaction temperature is 100° C.; and in the second mixed solution preparation step, a reaction time is 24 hours, and a reaction temperature is 100° C.

Further, in the first mixed solution preparation step and the second mixed solution preparation step, the catalyst is palladium acetate, tri-tert-butylphosphine tetrafluoroborate, sodium tert-butoxide and toluene.

Further, in the first mixed solution preparation step, the raw material of the first group, the 3,3'-dibromo-1,5,1',5'-tetramethyl-1,2,4,5-homotetradecene, the palladium acetate and the tri-tert-butylphosphine tetrafluoroborate are placed in the reaction vessel, the reaction vessel is placed in an argon atmosphere and the sodium tert-butoxide and deoxygenated toluene are added into the reaction vessel to obtain the first mixed solution.

Further, in the second mixed solution preparation step, the intermediate, the raw material of the second group, the palladium acetate and the tri-tert-butylphosphine tetrafluoroborate are placed together in the reaction vessel, the reaction vessel is placed in an argon atmosphere and the sodium tert-butoxide and deoxygenated toluene are added into the reaction vessel to obtain the first mixed solution.

Further, the first extraction step comprises: pouring the first mixed solution into ice water, and extracting multiple times with dichloromethane, and then combining the organic phases to obtain the heat activated delayed fluorescent monomolecular white light material; the second extraction step comprises: pouring the second mixed solution into ice water, and extracting multiple times with dichloromethane, and then combining the organic phases to obtain the heat activated delayed fluorescent monomolecular white light material.

The present invention also provides an organic electroluminescence device comprising a light emitting layer, wherein a light emitting dye of the light emitting layer is the heat-activated delayed fluorescent monomolecular white light material.

Beneficial Effect

The molecular system of the thermally activated delayed fluorescent monomolecular white light material of the present invention is a D1-A-D2 structure having different groups. The material arranges and combines D1 and D2 to make the D1-A-D2 structure forms an asymmetric structure, thereby having high white light luminescent properties.

In the final composition obtained by the synthesis method of the thermally activated delayed fluorescent monomolecular white light material of the invention, the synthesized heat activated delayed fluorescent monomolecular white light material accounts for a relatively high proportion. The method effectively improves the synthesis rate of the thermally activated delayed fluorescent monomolecular white light material. The thermally activated delayed fluorescent monomolecular white light material obtained by the present method has high white light luminescence properties.

The organic electroluminescent device of the invention adopts the thermally activated delayed fluorescent monomolecular white light material prepared by the invention, which has high luminous efficacy and long service life.

BRIEF DESCRIPTION OF DRAWINGS

In order to describe clearly the embodiment in the present disclosure or the prior art, the following will introduce the drawings for the embodiment shortly. Obviously, the following description is only a few embodiments, for the common technical personnel in the field it is easy to acquire some other drawings without creative work.

DETAILED DESCRIPTION OF PREFERRED EMBODIMENTS

Figure 1:
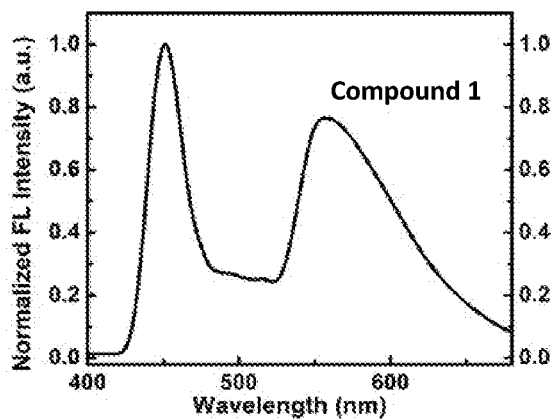
FIG. 1 is a photoluminescence spectrum of a target compound in embodiment 1.
Figure 2:
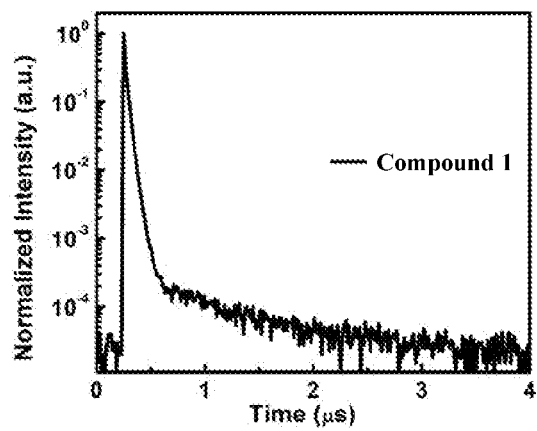
FIG. 2 is a transient spectrum diagram of the target compound in embodiment 1.

The embodiments of the present invention are described in detail below, and the examples of the embodiments are illustrated in the drawings, wherein the same or similar reference numerals indicate the same or similar elements or elements having the same or similar functions. The embodiments described below with reference to the drawings are intended to be illustrative of the invention and are not to be construed as limiting.

In the description of the present invention, it is to be understood that the azimuth or positional relationship indicated by the terms "center", "longitudinal", "horizontal", "length", "width", "thickness", "upper", "lower", "front", "back", "left", "right", "vertical", "horizontal", "top", "bottom", "inside", "outside", "clockwise", "counterclockwise", and the like is based on the orientation or positional relationship shown in the drawings. The terms of the invention are to be construed as illustrative only and not restrictive of the invention. Moreover, the terms "first" and "second" are used for descriptive purposes only and are not to be construed as indicating or implying a relative importance or implicitly indicating the number of technical features indicated. Thus, features defining "first" or "second" may include one or more of the described features either explicitly or implicitly. In the description of the present invention, the meaning of "a plurality" is two or more unless specifically and specifically defined otherwise.

In the description of the present invention, it should be noted that the terms "mount," "link," and "connect" are to be understood broadly unless otherwise specifically defined and defined. For example, they can be a fixed connection, a detachable connection, or an integral connection. They can be mechanical connections, electrical connections or can communicate with each other. They can be directly connected or indirectly connected through an intermediate medium. They can be the internal communication of two elements or the interaction of two elements. For those skilled in the art, the specific meanings of the above terms in the present invention can be understood on a case-by-case basis.

In the present invention, the first feature "on" or "under" the second feature may include direct contact of the first and second features, and may also include that the first and second features are not in direct contact but are contacted by additional features between them. Moreover, the first feature "above", "over" and "beyond" the second feature includes the first feature directly above and obliquely above the second feature, or merely indicating that the first feature is higher than the second feature. The first feature "below", "under" and "below" the second feature includes the first feature directly below and obliquely below the second feature, or merely indicating that the first feature is lower than the second feature.

The following disclosure provides many different embodiments or examples for implementing different structures of the present invention. In order to simplify the disclosure of the present invention, the components and arrangements of the specific examples are described below. Of course, they are merely examples and are not intended to limit the invention. In addition, the present invention may be repeated with reference to the numerals and/or reference numerals in the various examples, which are for the purpose of simplicity and clarity, and do not indicate the relationship between the various embodiments and/or arrangements discussed. Moreover, the present invention provides examples of various specific processes and materials, but one of ordinary skill in the art will recognize the use of other processes and/or the use of other materials.

The invention provides a thermally activated delayed fluorescent monomolecular white light material. The present invention researches into a thermally activated delayed fluorescence (TADF) material, and designs to synthesize a molecular system having D1-A-D2 structures with different donors. The invention provides the thermally activated delayed fluorescent monomolecular white light material obtained by synthesizing a raw material containing a first group, another raw material containing a second group and 3,3'-dibromo-1,5,1',5'-tetramethyl-1,2,4,5-homotetradecene, and a structure of the thermally activated delayed fluorescent monomolecular white light material is:

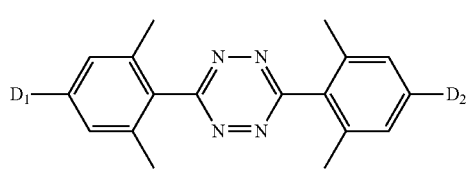

wherein, D1 is the first group, D2 is the second group, and the first group and the second group are asymmetric groups.

Further, in the structure, raw materials of the first group and the second group are selected from one of 9,9'-diphenylsilyl acridine, iminoguanidine, 3,6-dimethyl-spirosilane acridine, 3,6-dimethylcarbazole, and phenothiazine or acridone.

Specifically, a molecular structure of the first group and the second group is any one of the following, and the first group is different from the second group.

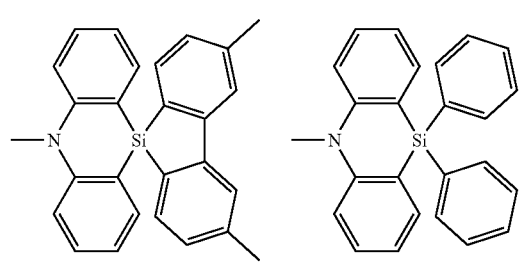

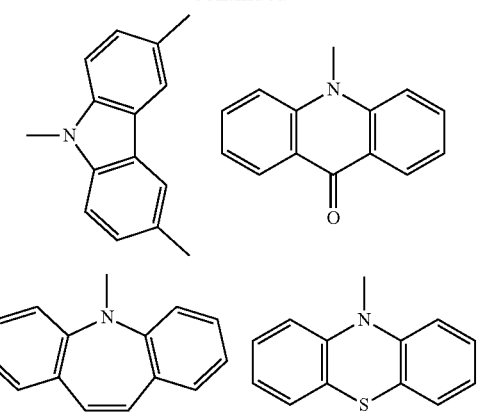

According to different materials selected from the first group and the second group, the structural of the finally generated fluorescent monomolecular white light material corresponds to one of the structures (1) to (9):

formula(1)

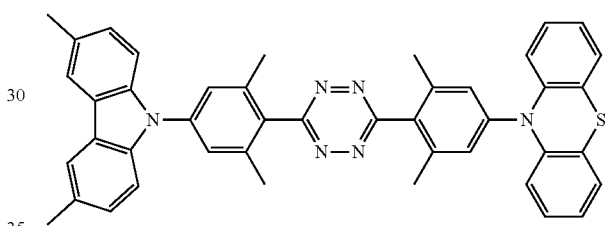

formula(2)

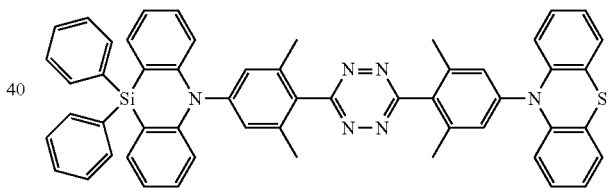

formula(3)

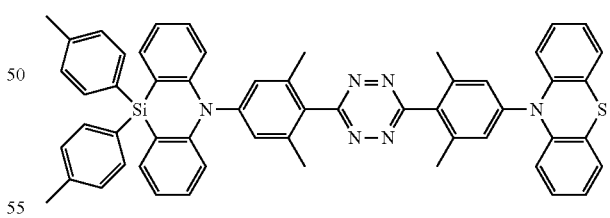

formula(4)

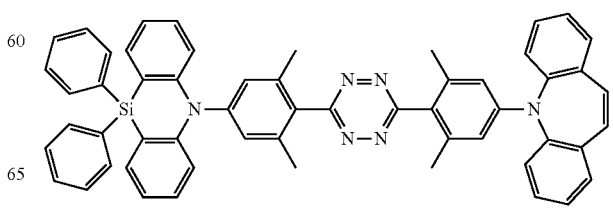

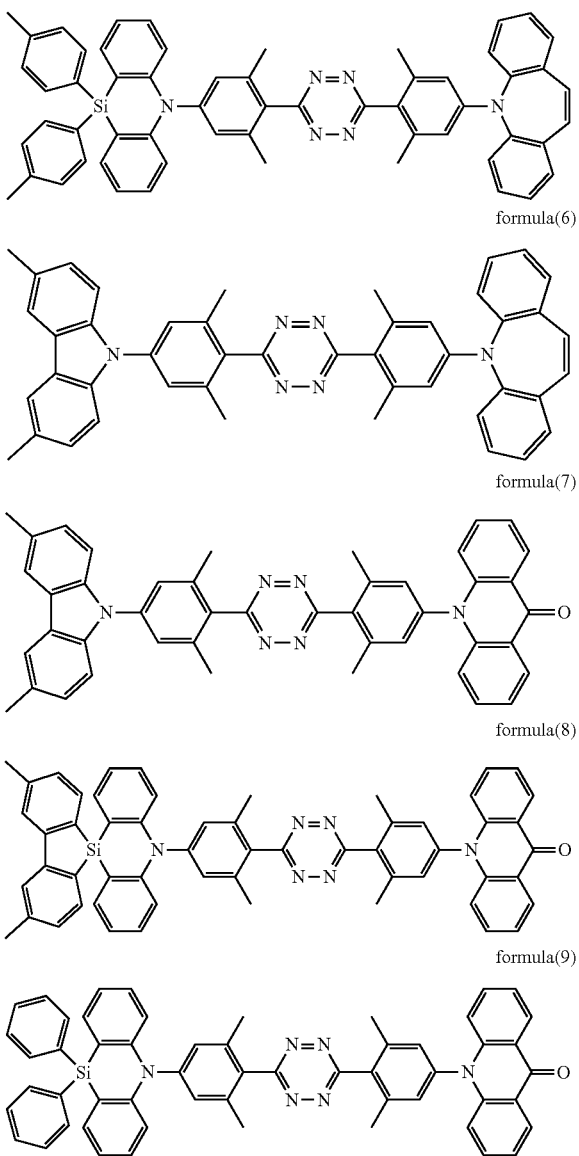

In order to more clearly illustrate the thermally activated delayed fluorescent monomolecular white light material of the present invention, specific embodiments 1-3 will be described in details below.

Embodiment 1

The thermally activated delayed fluorescent monomolecular white light material described in the formula (1) is synthesized, and the specific steps thereof are as follows.

A first mixed solution preparation step, comprising placing a raw material of a first group, 3,3'-dibromo-1,5,1',5'-tetramethyl-1,2,4,5-homotetradecene and a catalyst in a reaction vessel to be fully reacted to obtain a first mixed solution, wherein the first mixed solution comprises the raw material of the first group and an intermediate formed by the reaction of 3,3'-dibromo-1,5,1',5'-tetramethyl-1,2,4,5-homotetradecene. The raw material of the first group is selected from one of 9,9'-diphenylsilyl acridine, iminoguanidine, 3,6-dimethyl-spirosilane acridine, 3,6-dimethylcarbazole, and phenothiazine or acridone, and the preferred material is 3,6-dimethylcarbazole. A molar ratio of the raw material of the first group to 3,3'-dibromo-1,5,1',5'-tetramethyl-1,2,4,5-homotetradecene ranges from 1:1, in other embodiments, the molar ratio can be 1:3, 1:4 or 1:5. In the first mixed solution preparation step, the raw material of the first group (1.95 g, 10 mmol), the 3,3'-dibromo-1,5,1',5'-tetramethyl-1,2,4,5-homotetradecene (4.5 g, 10 mmol), the palladium acetate (90 mg, 0.4 mmol), and the tri-tert-butylphosphine tetrafluoroborate (0.34 g, 1.2 mmol) are placed in the reaction vessel, the reaction vessel is placed in an argon atmosphere and the sodium tert-butoxide NaOt-Bu (1.16 g, 12 mmol) and 60 ml deoxygenated toluene are added into the reaction vessel to obtain the first mixed solution by reacting at 110° C. for 24 hours.

A first extraction step, comprising cooling the first mixed solution to room temperature to extract the mixed solution and obtain the intermediate. In the first extraction step, pouring the first mixed solution into 200 ml ice water and extract it three times with dichloromethane. The target compound is initially purified by silica gel column chromatography to obtain an initial purified product. The volume ratio of the dichloromethane to the n-hexane is 1:5 during the silica gel column chromatography method. Finally, 3.37 g of a pale blue powder is isolated and purified, and the yield is 60%. The following analysis is performed on the pale blue powder prepared by the testing equipment according to the testing requirements, and the results of nuclear magnetic resonance and carbon spectra are: 1H NMR (300 MHz, CD2Cl2, δ): 8.43 (s, 2H), 7.85 (s, 2H), 7.83 (d, J=6.0 Hz, 2H), 7.41 (s, 2H), 7.38 (d, J=6.3 Hz, 2H), 2.57 (s, 12H), 2.46 (s, 6H). The result of mass spectrum is: MS (EI) m/z: [M]+calcd (theoretical value) for C32H28BrN5, 561.15; found (actual value), 561.10. The result of the elemental analysis is: Anal. (theoretical value) Calcd for C32H28BrN5: C, 68.33; H, 5.02; N, 12.45; found (actual value): C, 68.22; H, 4.98, N, 12.32.

A second mixed solution preparation step, comprising placing a raw material of a second group, the intermediate, and a catalyst in a reaction vessel to obtain a second mixed solution, wherein the second mixed solution comprises the intermediate and the raw material of the second group. Raw material of the second group is selected from one of 9,9'-diphenylsilyl acridine, iminoguanidine, 3,6-dimethyl-spirosilane acridine, 3,6-dimethylcarbazole, and phenothiazine or acridone, and the preferred material is phenothiazine. A molar ratio of the raw material of the second group to 3,3'-dibromo-1,5,1',5'-tetramethyl-1,2,4,5-homotetradecene ranges from 1:1, in other embodiments, the molar ratio can be 1:3, 1:4 or 1:5. In the second mixed solution preparation step, the intermediate 1 (1.0 g, 5 mmol), the raw material of the second group (2.8 g, 5 mmol), the palladium acetate (45 mg, 0.2 mmol) and the tri-tert-butylphosphine tetrafluoroborate (0.17 g, 0.6 mmol) are placed together in the reaction vessel, the reaction vessel is placed in an argon atmosphere and the sodium tert-butoxide NaOt-Bu (0.58 g, 6 mmol) and 60 mL deoxygenated toluene are added into the reaction vessel to obtain the second mixed solution by reacting at 110° C. for 24 hours.

A second extraction step, comprising cooling the second mixed solution to room temperature, wherein the second mixed solution is extracted to obtain a target compound, and the target compound is isolated and purified to obtain the thermally activated delayed fluorescent monomolecular white light material. In the second extraction step, pouring the second mixed solution into 200 mL ice water and extract it three times with dichloromethane. The target compound is initially purified by silica gel column chromatography to obtain an initial purified product. The volume ratio of the dichloromethane to the n-hexane is 1:5 during the silica gel column chromatography method. Finally, 1.7 g of a white powder is isolated and purified, and the yield is 50%. The following analysis is performed on the white powder prepared by the testing equipment according to the testing requirements, and the results of nuclear magnetic resonance and carbon spectra are: 11H NMR (300 MHz, CD2Cl2, δ): 8.45 (s, 2H), 7.86 (s, 2H), 7.83 (d, J=6.0 Hz, 2H), 7.41 (s, 2H), 7.38 (d, J=6.3 Hz, 2H), 7.21 (d, J=6.3 Hz, 2H), 7.16-6.93 (m, 6H), 2.57 (s, 12H), 2.46 (s, 6H). The result of mass spectrum is: MS (EI) m/z: [M]+calcd (theoretical value) for C44H36N6S, 680.27; found (actual value), 680.10. The result of the elemental analysis is: Anal. (theoretical value) Calcd for C44H36N6S: C, 77.62; H, 5.33; N, 12.34; found (actual value): C77.83; H, 5.34; N, 12.39.

The chemical reaction process of the method of embodiment 1 is as follows:

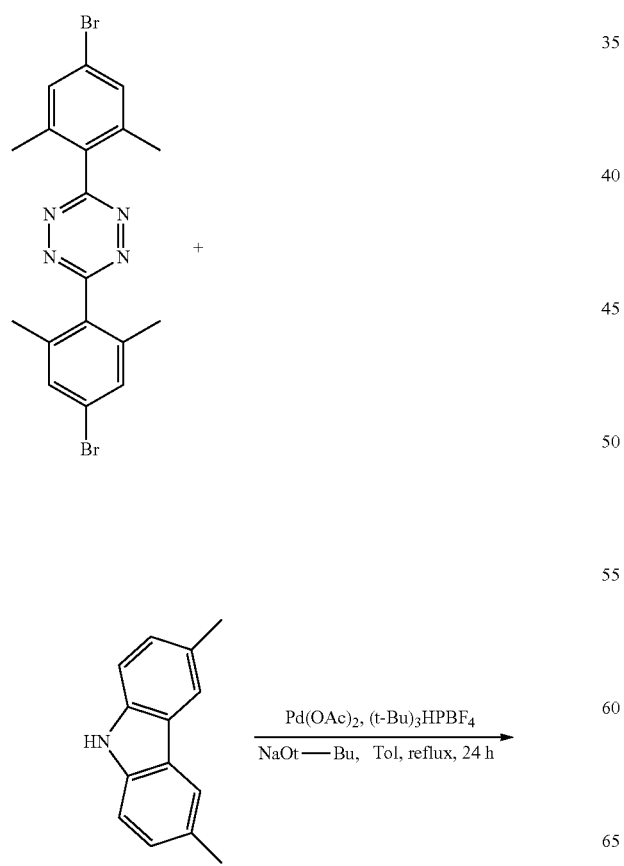

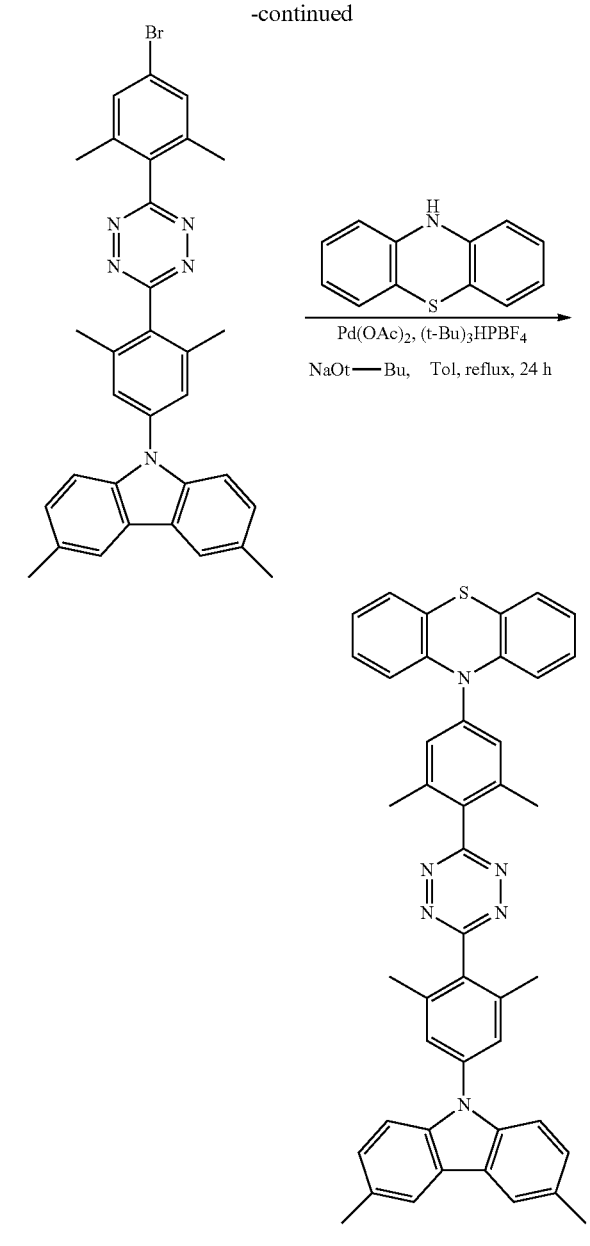

Embodiment 2

The thermally activated delayed fluorescent monomolecular white light material described in the formula (4) is synthesized, and the specific steps thereof are as follows.

A first mixed solution preparation step, comprising placing a raw material of a first group, 3,3'-dibromo-1,5,1',5'-tetramethyl-1,2,4,5-homotetradecene and a catalyst in a reaction vessel to be fully reacted to obtain a first mixed solution, wherein the first mixed solution comprises the raw material of the first group and an intermediate formed by the reaction of 3,3'-dibromo-1,5,1',5'-tetramethyl-1,2,4,5-homotetradecene. Raw material of the first group is selected from one of 9,9'-diphenylsilyl acridine, iminoguanidine, 3,6-dimethyl-spirosilane acridine, 3,6-dimethylcarbazole, and phenothiazine or acridone, and the preferred material is 9,9'-diphenylsilyl acridine. A molar ratio of the raw material of the first group to 3,3'-dibromo-1,5,1',5'-tetramethyl-1,2, 4,5-homotetradecene ranges from 1:1, in other embodiments, the molar ratio can be 1:3, 1:4 or 1:5. In the first mixed solution preparation step, the raw material of the first group (3.5 g, 10 mmol), the 3,3'-dibromo-1,5,1',5'-tetramethyl-1,2,4,5-homotetradecene (4.5 g, 10 mmol), the palladium acetate (90 mg, 0.4 mmol), and the tri-tert-butylphosphine tetrafluoroborate (0.34 g, 1.2 mmol) are placed in the reaction vessel, the reaction vessel is placed in an argon atmosphere and the sodium tert-butoxide NaOt-Bu (1.16 g, 12 mmol) and 60 ml deoxygenated toluene are added into the reaction vessel to obtain the first mixed solution by reacting at 110° C. for 24 hours.

A first extraction step, comprising cooling the first mixed solution to room temperature to extract the mixed solution and obtain the intermediate. In the first extraction step, pouring the first mixed solution into 200 mL ice water and extract it three times with dichloromethane. A target compound is initially purified by silica gel column chromatography to obtain an initial purified product. The volume ratio of the dichloromethane to the n-hexane is 1:5 during the silica gel column chromatography method. Finally, 3.37 g of a pale blue powder is isolated and purified, and the yield is 60%. The following analysis is performed on the pale blue powder prepared by the testing equipment according to the testing requirements, and the results of nuclear magnetic resonance and carbon spectra are: 1H NMR (300 MHz, CD2Cl2, δ): 7.42-7.38 (m, 14H), 7.34 (s, 2H), 7.30-7.28 (m, 4H), 7.03 (t, J=6.9 Hz, 2H), 2.57 (s, 12H), 2.57 (s, 12H). The result of mass spectrum is: MS (EI) m/z: [M]+calcd (theoretical value) for C42H34BrN5Si, 445.97; found (actual value), 445.97. The result of the elemental analysis is: Anal. (theoretical value) Calcd for C42H34BrN5Si: C, 70.38; H, 4.78; N, 9.77; found (actual value): C, 70.22; H, 4.68; N, 9.56.

A second mixed solution preparation step, comprising placing a raw material of a second group, the intermediate and a catalyst in a reaction vessel to obtain a second mixed solution, wherein the second mixed solution comprises the intermediate and the raw material of the second group. Raw material of the second group is selected from one of 9,9'-diphenylsilyl acridine, iminoguanidine, 3,6-dimethyl-spirosilane acridine, 3,6-dimethylcarbazole, and phenothiazine or acridone, and the preferred material is iminoguanidine. A molar ratio of the raw material of the second group to 3,3'-dibromo-1,5,1',5'-tetramethyl-1,2,4,5-homotetradecene ranges from 1:1, in other embodiments, the molar ratio can be 1:3, 1:4 or 1:5. In the second mixed solution preparation step, the intermediate 2 (2.86 g, 4 mmol), the raw material of the second group (0.77 g, 4 mmol), the palladium acetate (38 mg, 0.217 mmol) and the tri-tert-butylphosphine tetrafluoroborate (0.14 g, 0.5 mmol) are placed together in the reaction vessel, the reaction vessel is placed in an argon atmosphere and the sodium tert-butoxide NaOt-Bu (0.48 g, 5 mmol) and 60 mL deoxygenated toluene are added into the reaction vessel to obtain the second mixed solution by reacting at 110° C. for 24 hours.

A second extraction step, comprising cooling the second mixed solution to room temperature, wherein the second mixed solution is extracted to obtain a target compound, and the target compound is isolated and purified to obtain the thermally activated delayed fluorescent monomolecular white light material. In the second extraction step, pouring the second mixed solution into 200 mL ice water and extract it three times with dichloromethane. The target compound is initially purified by silica gel column chromatography to obtain an initial purified product. The volume ratio of the dichloromethane to the n-hexane is 1:5 during the silica gel column chromatography method. Finally, 1.2 g of a white powder is isolated and purified, and the yield is 36%. The following analysis is performed on the white powder prepared by the testing equipment according to the testing requirements, and the results of nuclear magnetic resonance and carbon spectra are: 1H NMR (300 MHz, CD2Cl2, δ): 7.52-7.46 (m, 12H), 7.34 (s, 2H), 7.31 (s, 2H), 7.29-7.23 (m, 4H), 7.19-7.03 (m, 10H), 6.99 (s, 2H), 2.57 (s, 12H). The result of mass spectrum is: MS (EI) m/z: [M]+calcd (theoretical value) for C56H44N6Si, 828.34; found (actual value), 828.30. The result of the elemental analysis is: Calcd. (theoretical value) for C56H44N6Si: C, 81.23, H, 5.35; N, 10.14; found (actual value): C, 81.21; H, 5.34; N, 10.09.

The chemical reaction process of the method of embodiment 2 is as follows:

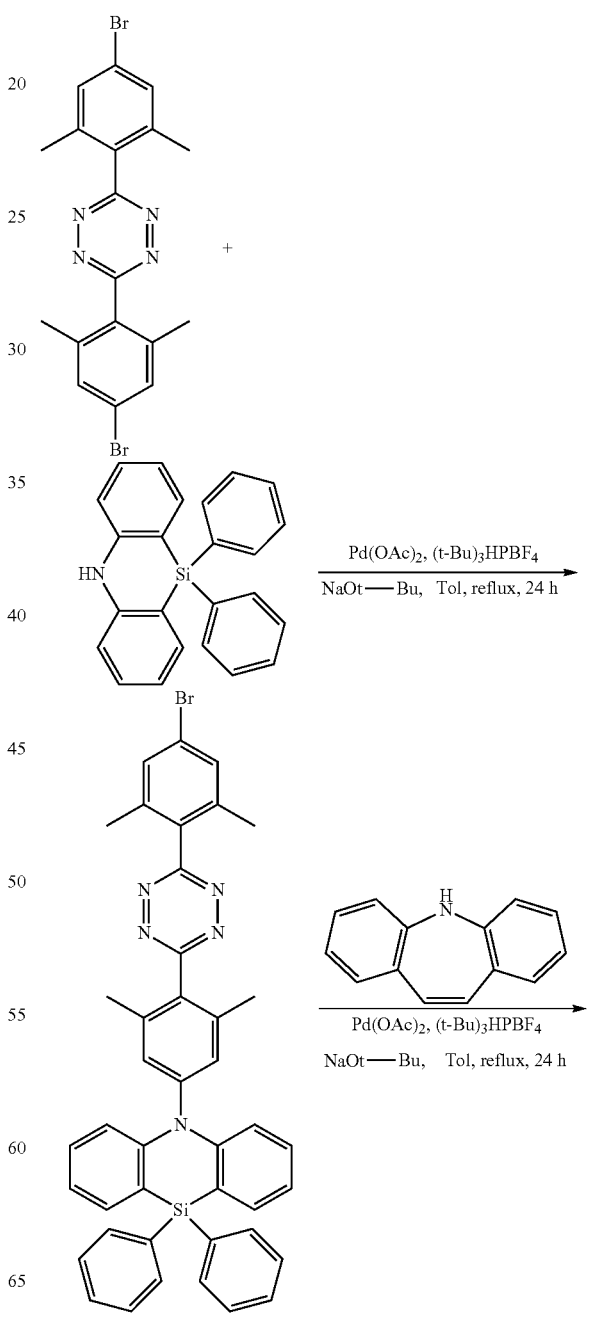

-continued

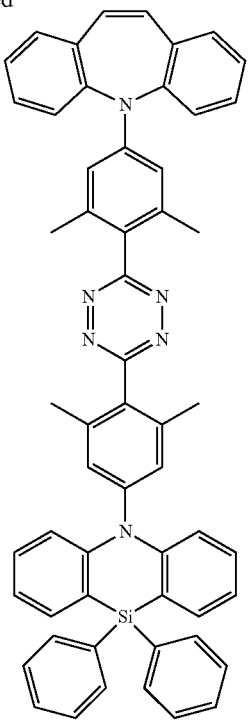

Embodiment 3

The thermally activated delayed fluorescent monomolecular white light material described in the formula (8) is synthesized, and the specific steps thereof are as follows.

A first mixed solution preparation step, comprising placing a raw material of a first group, 3,3'-dibromo-1,5,1',5'-tetramethyl-1,2,4,5-homotetradecene, and a catalyst in a reaction vessel to be fully reacted to obtain a first mixed solution, wherein the first mixed solution comprises the raw material of the first group and an intermediate formed by the reaction of 3,3'-dibromo-1,5,1',5'-tetramethyl-1,2,4,5-homotetradecene. Raw material of the first group is selected from one of 9,9'-diphenylsilyl acridine, iminoguanidine, 3,6-dimethyl-spirosilane acridine, 3,6-dimethylcarbazole, and phenothiazine or acridone, and the preferred material is 3,6-dimethyl-spirosilane acridine. A molar ratio of the raw material of the first group to 3,3'-dibromo-1,5,1',5'-tetramethyl-1,2,4,5-homotetradecene ranges from 1:1, in other embodiments, the molar ratio can be 1:3, 1:4 or 1:5. In the first mixed solution preparation step, the 3,3'-dibromo-1,5,1',5'-tetramethyl-1,2,4,5-homotetradecene (4.5 g, 10 mmol), 3,6-dimethyl-spirosilane acridine (3.75 g, 10 mmol), the palladium acetate (90 mg, 0.4 mmol), and the tri-tert-butylphosphine tetrafluoroborate (0.34 g, 1.2 mmol) are placed in the reaction vessel, the reaction vessel is placed in an argon atmosphere and the sodium tert-butoxide NaOt-Bu (1.16 g, 12 mmol) and 60 ml deoxygenated toluene are added into the reaction vessel to obtain the first mixed solution by reacting at 110° C. for 24 hours.

A first extraction step, comprising cooling the first mixed solution to room temperature to extract the mixed solution and obtain the intermediate. In the first extraction step, pouring the first mixed solution into 200 mL ice water and extract it three times with dichloromethane. The target compound is initially purified by silica gel column chromatography to obtain an initial purified product. The volume ratio of the dichloromethane to the n-hexane is 1:5 during the silica gel column chromatography method. Finally, 4.0 g of a pale blue powder is isolated and purified, and the yield is 54%. The following analysis is performed on the pale blue powder prepared by the testing equipment according to the testing requirements, and the results of nuclear magnetic resonance and carbon spectra are: 1H NMR (300 MHz, CD2Cl2, δ): 8.43 (s, 2H), 7.88 (s, 2H), 7.60 (d, J=6.3 Hz, 2H), 7.46-7.21 (m, 8H), 7.09-6.98 (m, 6H), 2.57 (s, 12H). The result of mass spectrum is: MS (EI) m/z: [M]+calcd (theoretical value) for C44H36BrN5Si, 741.19; found (actual value), 741.10. The result of the elemental analysis is: Calcd (theoretical value) for C44H36BrN5Si: C, 71.15; H, 4.89; N, 9.43; found (actual value): C, 71.10; H, 4.76; N, 9.32.

A second mixed solution preparation step, comprising placing a raw material of a second group, the intermediate, and a catalyst in a reaction vessel to obtain a second mixed solution, wherein the second mixed solution comprises the intermediate and the raw material of the second group. Raw material of the second group is selected from one of 9,9'-diphenylsilyl acridine, iminoguanidine, 3,6-dimethyl-spirosilane acridine, 3,6-dimethylcarbazole, and phenothiazine or acridone, and the preferred material is acridone. A molar ratio of the raw material of the second group to 3,3'-dibromo-1,5,1',5'-tetramethyl-1,2,4,5-homotetradecene ranges from 1:1, in other embodiments, the molar ratio can be 1:3, 1:4 or 1:5. In the second mixed solution preparation step, the intermediate 3 (3.7 g, 5 mmol), the acridone (1.0, 5 mmol), the palladium acetate (45 mg, 0.2 mmol), and the tri-tert-butylphosphine tetrafluoroborate (0.17 g, 0.6 mmol) are placed together in the reaction vessel, the reaction vessel is placed in an argon atmosphere and the sodium tert-butoxide NaOt-Bu (0.48 g, 5 mmol) and 60 mL deoxygenated toluene are added into the reaction vessel to obtain the second mixed solution by reacting at 110° C. for 24 hours.

A second extraction step, comprising cooling the second mixed solution to room temperature, wherein the second mixed solution is extracted to obtain a target compound, and the target compound is isolated and purified to obtain the thermally activated delayed fluorescent monomolecular white light material. In the second extraction step, pouring the second mixed solution into 200 mL ice water and extract it three times with dichloromethane. The target compound is initially purified by silica gel column chromatography to obtain an initial purified product. The volume ratio of the dichloromethane to the n-hexane is 1:5 during the silica gel column chromatography method. Finally, 1.1 g of a white powder is isolated and purified, and the yield is 26%. The following analysis is performed on the white powder prepared by the testing equipment according to the testing requirements, and the results of nuclear magnetic resonance and carbon spectra are: 1H NMR (300 MHz, CD2Cl2, δ): 7.88 (s, 2H), 7.66 (d, J=6.3 Hz, 2H), 7.60 (d, J=6.9 Hz, 2H), 7.50-7.23 (m, 16H), 7.17 (t, J=6.3 Hz, 2H), 7.03 (t, J=6.6 Hz, 2H), 2.57 (s, 12H), 2.46 (s, 6H). The result of mass spectrum is: MS (EI) m/z: [M]+calcd (theoretical value) for C57H44N6OSi, 856.33; found (actual value), 856.23. The result of the elemental analysis is: Calcd. (theoretical value) for C57H44N6OSi: C, 79.88; H, 5.17; N, 9.81; found (actual value): C79.83; H, 5.14; N, 9.69.

The chemical reaction process of the method of embodiment 3 is as follows:

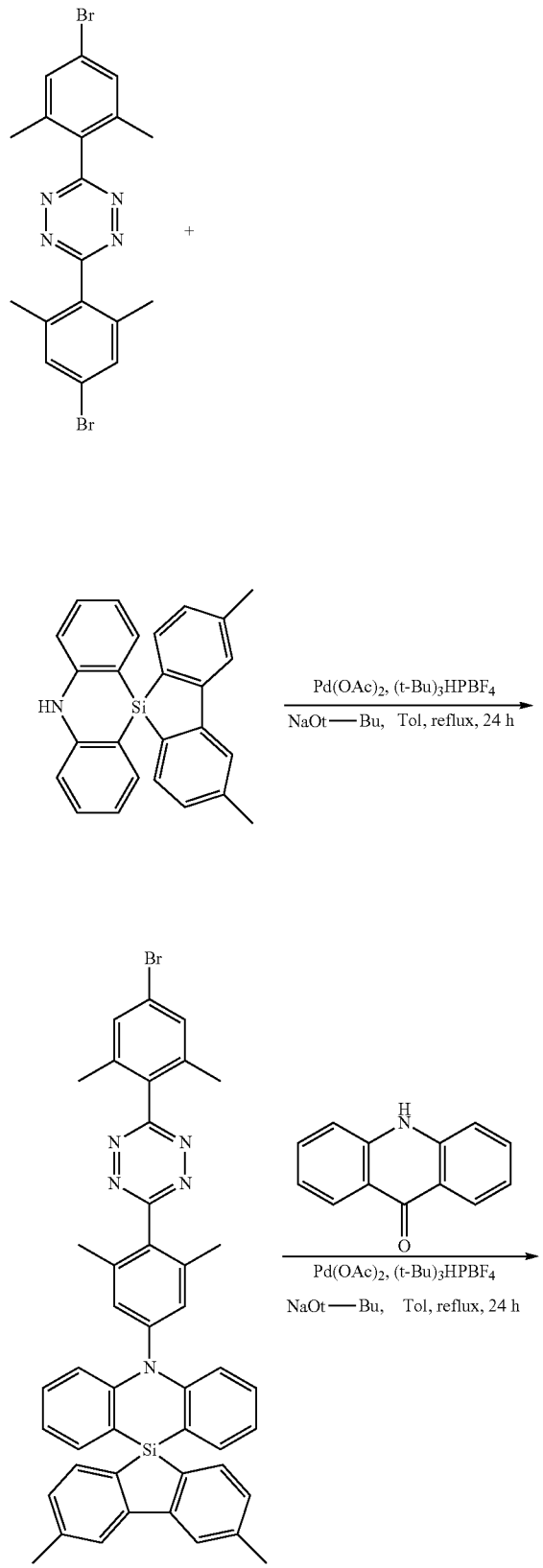

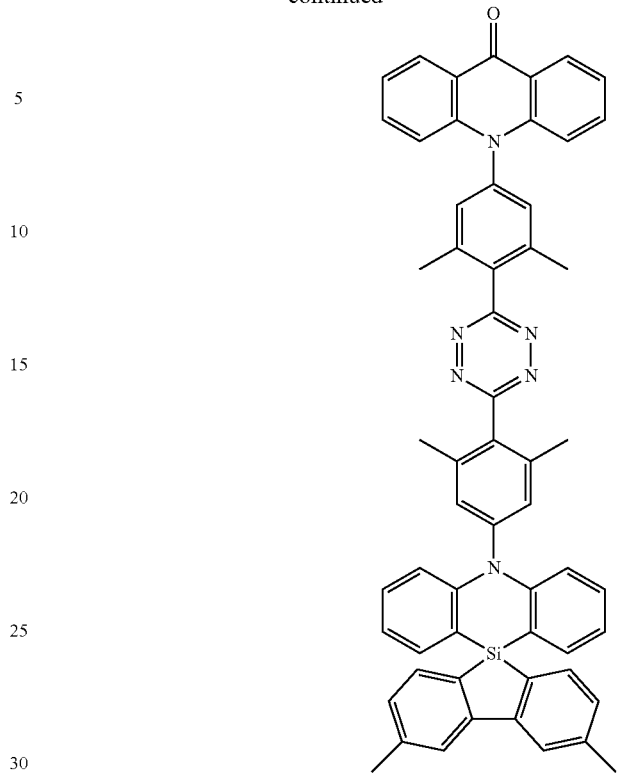

Other structures of the thermally activated delayed fluorescent monomolecular white light material, as shown in formula (2), formula (9), etc., the preparation methods thereof are described in the methods of embodiment 1-3. The main preparation steps are the same, the only difference is that the materials selected for the first group and the second group are different, and therefore will not be further described.

Application Embodiment

The thermally activated delayed fluorescent monomolecular white light materials disclosed in the present invention can be applied to organic electroluminescent devices, and in particular, to light emitting layers. Monomolecular white light materials are considered to be the most potential white light illumination materials because of their excellent luminescent properties and no phase separation.

The present invention deeply studies the thermally activated delayed fluorescence (TADF) material, and designs to synthesize a molecular system having D1-A-D2 structures with different donors. D1 and D2 are arranged in combination to select molecules having excellent white light luminescence properties. In order to apply the white light molecules to a display device, general displays include organic electroluminescent devices, and the light emitting layers are disposed in the organic electroluminescent devices. The application of the present invention will be further described in an application embodiment with an organic electroluminescent device.

Figure 3:
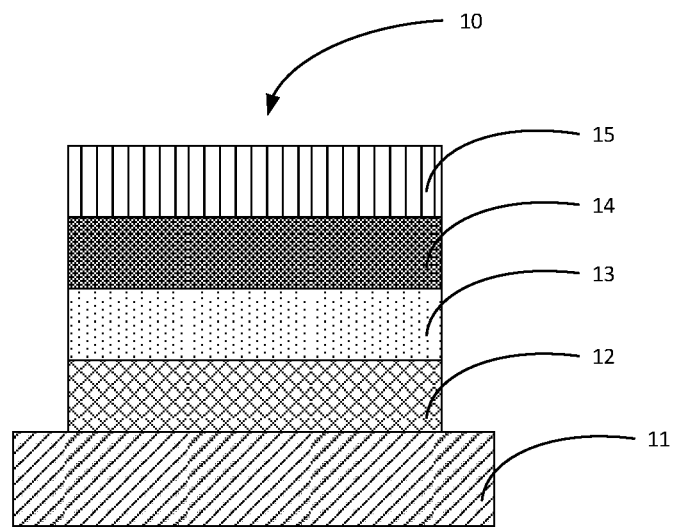
FIG. 3 is a cross-sectional diagram of a structure of an organic light emitting device of embodiment 1.

As shown in FIG. 3, the organic electroluminescent device 10 includes a substrate layer 11, a first functional layer 12, a light emitting layer 13, a second functional layer 14, and a cathode layer 15. The substrate layer 11 is conductive glass. The first functional layer 12 is a hole transport layer and is attached to one side of the substrate 11. The light emitting layer 13 is attached to a side of the first functional layer 12 away from the substrate 11. The second functional layer 14 is an electron transport layer, and is attached to a side of the light emitting layer 13 away from the first functional layer 12. The cathode layer 15 is attached to a side of the second functional layer 14 away from the light emitting layer 13.

Material of the substrate layer 11 can be glass and/or conductive glass (indium tin oxide, ITO), and its thickness generally ranges from 45 to 55 nm. Material of the hole transport layer can be one of poly 3,4-ethylenedioxythiophene, polystyrene sulfonate, and PEDOT:PSS, and its thickness generally ranges from 45 to 55 nm. Material of the electron transport layer can be 1,3,5-tris(3-(3-pyridyl)phenyl)benzene or TmPyPB, and its thickness generally ranges from 35 to 45 nm. Material of the cathode layer can be lithium fluoride or aluminum, and its thickness generally ranges from 95 to 105 nm. Material of the light emitting layer 13 is the thermally activated delayed fluorescent monomolecular white light material (40 nm) of the present invention, which is formed by vapor deposition under high vacuum conditions.

In order to fully explain the performance of the organic electroluminescent device of the present invention, performance measurement is performed. Current-luminance-voltage characteristics of the organic electroluminescent device are performed by a Keithley source measurement system (Keithley 2400 Sourcemeter, Keithley 2000 Currentmeter) with a calibrated silicon photodiode. The electroluminescence spectrum is measured by a French JY SPEX CCD3000 spectrometer. All measurements are done at room temperature in the atmosphere. The performance data of the device is shown in Table 1 below:

Table 1 shows various performance parameters such as maximum brightness and starting voltage of the organic electroluminescent device.

| Device | Maximum brightness (cd/m$^2$) | Vth (V) | CIE | Maximum external quantum efficacy (%) |
|---|---|---|---|---|
| Device 1 | 986 | 7.3 | (0.24, 0.3) | 7.3 |
| Device 2 | 700 | 7.0 | (0.32, 0.3) | 6.0 |

As shown in Table 1, device 1 is the organic electroluminescent device of the present invention, and device 2 is a comparative device. The spectral CIE coordinates of device 1 and device 2 are both white light. It can be seen that the device 1 provided by the present invention has higher maximum brightness, and the quantum efficacy is also improved as compared with device 2.

As is understood by persons skilled in the art, the foregoing preferred embodiments of the present disclosure are illustrative rather than limiting of the present disclosure. It is intended that they cover various modifications and that similar arrangements be included in the spirit and scope of the present disclosure, the scope of which should be accorded the broadest interpretation so as to encompass all such modifications and similar structures.

What is claimed is:

1. A thermally activated delayed fluorescent monomolecular white light material, wherein the thermally activated delayed fluorescent monomolecular white light material is obtained by synthesizing a raw material containing a first group, another raw material containing a second group and 3,3'-dibromo-1,5,1',5'-tetramethyl-1,2,4,5-homotetradecene, and a structure of the thermally activated delayed fluorescent monomolecular white light material is:

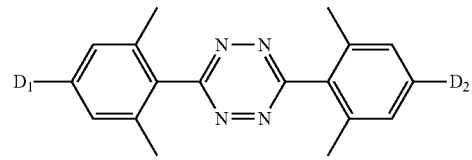

wherein, D1 is the first group, D2 is the second group, and the first group and the second group are asymmetric groups.

2. The thermally activated delayed fluorescent monomolecular white light material according to claim 1, wherein, in the structure, raw materials of the first group and the second group are selected from one of 9,9'-diphenylsilyl acridine, iminoguanidine, 3,6-dimethyl-spirosilane acridine, 3,6-dimethylcarbazole, and phenothiazine or acridone.

3. A method for synthesizing a thermally activated delayed fluorescent monomolecular white light material, comprising the steps of:
a first mixed solution preparation step, comprising placing a raw material of a first group, 3,3'-dibromo-1,5,1',5'-tetramethyl-1,2,4,5-homotetradecene, and a catalyst in a reaction vessel to be fully reacted to obtain a first mixed solution, wherein the first mixed solution comprises the raw material of the first group and an intermediate formed by the reaction of 3,3'-dibromo-1,5,1',5'-tetramethyl-1,2,4,5-homotetradecene;
a first extraction step, comprising cooling the first mixed solution to room temperature to extract the mixed solution and obtain the intermediate;
a second mixed solution preparation step, comprising placing a raw material of a second group, the intermediate, and a catalyst in a reaction vessel to obtain a second mixed solution, wherein the second mixed solution comprises the intermediate and the raw material of the second group;
a second extraction step, comprising cooling the second mixed solution to room temperature, wherein the second mixed solution is extracted to obtain a target compound, and the target compound is isolated and purified to obtain the thermally activated delayed fluorescent monomolecular white light material.

4. The method of synthesizing the thermally activated delayed fluorescent monomolecular white light material according to claim 3, wherein, the raw materials of the first group and the second group are selected from one of 9,9'-diphenylsilyl acridine, iminoguanidine, 3,6-dimethyl-spirosilane acridine, 3,6-dimethylcarbazole, and phenothiazine or acridone; and
a molar ratio of the raw material of the first group to 3,3'-dibromo-1,5,1',5'-tetramethyl-1,2,4,5-homotetradecene ranges from 1:1 to 1:5, and a molar ratio of the raw material of the second group to the intermediate ranges from 1:1 to 1:5.

5. The method of synthesizing the thermally activated delayed fluorescent monomolecular white light material according to claim 3, wherein,
in the first mixed solution preparation step, reaction time is 24 hours, and a reaction temperature is 100° C.; and
in the second mixed solution preparation step, reaction time is 24 hours, and a reaction temperature is 100° C.

6. The method of synthesizing the thermally activated delayed fluorescent monomolecular white light material according to claim 3, wherein,
in the first mixed solution preparation step and the second mixed solution preparation step, the catalyst is palladium acetate, tri-tert-butylphosphine tetrafluoroborate, sodium tert-butoxide, and toluene.

7. The method of synthesizing the thermally activated delayed fluorescent monomolecular white light material according to claim 6, wherein,
in the first mixed solution preparation step, the raw material of the first group, the 3,3'-dibromo-1,5,1',5'-tetramethyl-1,2,4,5-homotetradecene, the palladium acetate, and the tri-tert-butylphosphine tetrafluoroborate are placed in the reaction vessel, the reaction vessel is placed in an argon atmosphere and the sodium tert-butoxide and deoxygenated toluene are added into the reaction vessel to obtain the first mixed solution.

8. The method of synthesizing the thermally activated delayed fluorescent monomolecular white light material according to claim 6, wherein,
in the second mixed solution preparation step, the intermediate, the raw material of the second group, the palladium acetate, and the tri-tert-butylphosphine tetrafluoroborate are placed together in the reaction vessel, the reaction vessel is placed in an argon atmosphere and the sodium tert-butoxide and deoxygenated toluene are added into the reaction vessel to obtain the second mixed solution.

9. The method of synthesizing the thermally activated delayed fluorescent monomolecular white light material according to claim 4, wherein,
the first extraction step comprises: pouring the first mixed solution into ice water, and extracting multiple times with dichloromethane, and then combining the organic phases to obtain the intermediate;
the second extraction step comprises: pouring the second mixed solution into ice water, and extracting multiple times with dichloromethane, and then combining the organic phases to obtain the thermally activated delayed fluorescent monomolecular white light material.

10. An organic electroluminescence device comprising a light emitting layer, wherein a light emitting dye of the light emitting layer is the thermally activated delayed fluorescent monomolecular white light material of claim 1.

* * * * *